United States Patent [19]

Yamashina

[11] Patent Number: 5,073,493
[45] Date of Patent: Dec. 17, 1991

[54] MONOCLONAL ANTIBODY NKY13
[75] Inventor: Ikuo Yamashina, Kyoto, Japan
[73] Assignee: Ikuo Yamashina, Kyoto, Japan
[21] Appl. No.: 200,524
[22] Filed: May 26, 1988
[30] Foreign Application Priority Data May 29, 1987 [JP] Japan .................. 62-137012

[51] Int. Cl.$^5$ ............ C12N 5/20; C12N 15/02; C07K 15/28; C12P 21/08
[52] U.S. Cl. ............ 435/240.27; 530/327; 435/70.21; 435/172.2
[58] Field of Search .......... 530/387; 435/240.27, 435/172.2, 70.21

[56] References Cited

PUBLICATIONS

Schlorn et al., Cancer Res. 46:3225-28 1986.
Magnani et al., J. Biol. Chem. 257(22):14365-9, 1982.
Fukushi et al., Biochemistry 25:2859-66, 1986.
Wieruszeski et al., Carbohydrate Res. 137:127-38, 1985.
Mansson et al., Biochimica et Biophysicci Acta 834: 110-117, 1985.
Kipps et al., pp. 108.1-108.9 in Weir et al., Eds. "Handbook of Expt'l. Immunology", vol. 4, Blackwell Sci. Publ., 1986.
Brockhaus et al., Vox Sang. 48:34-38, 1985.

Primary Examiner—Esther L. Kepplinger
Assistant Examiner—Paula Hutzell
Attorney, Agent, or Firm—Birch, Stewart, Kolasch & Birch

[57] ABSTRACT

Monoclonal antibody NKY13 recognizing sugar chains of mucin-type glycoproteins secreted by cancer cells, for example, the following sugar chains, and hydridoma producing it:

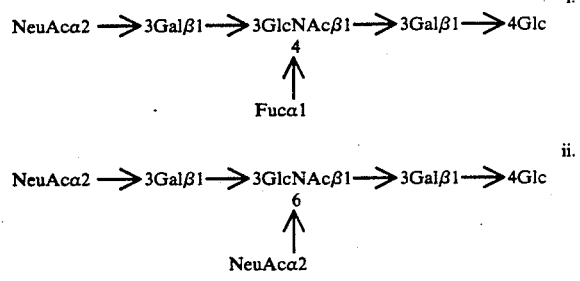

The monoclonal antibody NKY13 renders it possible to make highly sensitive judgements in the serodiagnosis of such cancers as colon cancer, stomach cancer and pancreas cancer.

2 Claims, 3 Drawing Sheets

MONOCLONAL ANTIBODY NKY13

BACKGROUND OF THE INVENTION

Field of the Invention

This invention relates to a monoclonal antibody NKY13 which recognizes sugar chains of glycoproteins secreted by cancer cells and to a hybridoma which secretes the NKY13. More specifically, this invention pertains to the monoclonal antibody NKY13 which reacts human intestinal cancer cells and normal epithelial cells of human intestines and also with sugar chains containing sialic acid, especially with sugar chains containing the following structures and also to the hybridoma which stably proliferates in rat's abdominal cavity and secretes NKY13.

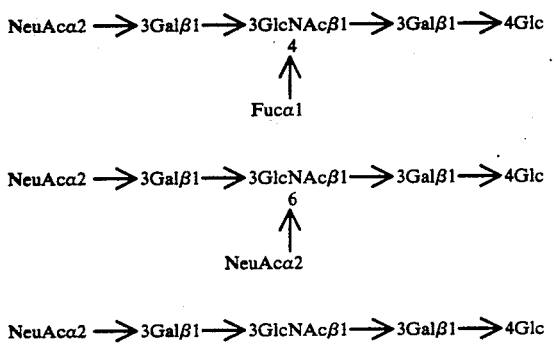

DESCRIPTION OF RELATED ART

It has been recognized that on the surface of cells there are complex carbohydrates such as glycoprotein, glycolipid and proteoglycan, whose sugar chains are altered as normal cells are transformed into cancer cells. Elucidation of the mutation, that is, the change of sugar chain structure has been attempted mainly by chemically analyzing the sugar chain. However, it has become possible to obtain such a monoclonal antibody as specifically binding to a variety of sugar chains on the surface of a cancer cell since 1975 when Köhler and Milstein established the method to make a hybridoma and obtain a monoclonal antibody therefrom. Recently, it has been reported that many of monoclonal antibodies recognizing cancer-associated antigens recognize sugar chains and, therefore, the significance of a monoclonal antibody recognizing a cancer-associated sugar antigen has been pointed out and, further, some sugar chain structures of the cancer-associated antigens have been determined. It is believed that such monoclonal antibodies play a significant role in a clinical field such as diagnosis, an inspection and an therapy of cancer as well as in studies on cancer. Indeed, CA19-9, which is one of cancer-associated sugar antigens, in sera of cancer patients can be assayed by using a monoclonal antibody NS19-9 specifically recognizing CA19-9 (J. Magnani et al., J. Biol. Chem. 257, 14365 (1982)), which has been effectively utilized in a diagnosis of pancreatic cancer.

Most of conventional monoclonal antibodies have been prepared according to the usual method that either cancer cells or mixtures of glycolipids extracted from cancer cells are used as immunogens with suitable adjuvants and from resulting antibodies are selected such antibodies that bind to cancer cells but do not bind to corresponding normal cells. However, since the cancer-associated sugar chain antigens appearing in sera of cancer patients are mucin-type glycoproteins that are synthesized in and secreted from cancer cells, there has been a demand for the production of antibodies toward sugar chains of such glycoproteins.

Previously, the present inventor invented a method for the titration of antibodies toward the sugar chains of glycoproteins with the use of immobilized glycopeptides (Japanese Patent Application No. 61-57772). By using this method, those recognizing sugar chains can be effectively selected from a number of monoclonal antibodies that are prepared with the use of cancer cells as immunogens. In this invention, from such monoclonal antibodies those recognizing sugar chains of mucin-type glycoproteins were selected and their significance was indicated.

SUMMARY

This invention relates to a monoclonal antibody NKY13 which recognizes sugar chains of glycoproteins secreted by cancer cells and to a hybridoma which secretes the NKY13. More specifically, the monoclonal antibody NKY13 reacts also with sugar chains containing sialic acid, especially with sugar chains containing the following structures:

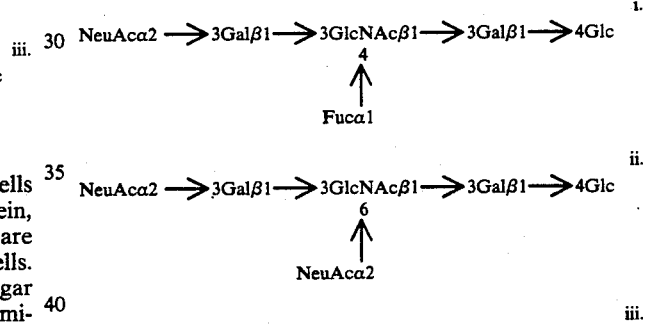

The monoclonal antibody NKY13 of this invention renders it possible to make highly sensitive judgements in the serodiagnosis of such cancers as colon cancer, stomach cancer and pancreas cancer. Moreover, the hybridoma which secretes the said antibody can be stored for a long period and proliferates stably in the abdominal cavities of mice so that it has become possible to supply said monoclonal antibody whenever necessary. Therefore, the monoclonal antibody NKY13 of this invention and the hybridoma secreting said antibody are considered to provide a very remarkable effect for the diagnosis and treatment of cancers.

DETAILED DESCRIPTION OF THE INVENTION

Figure 1:
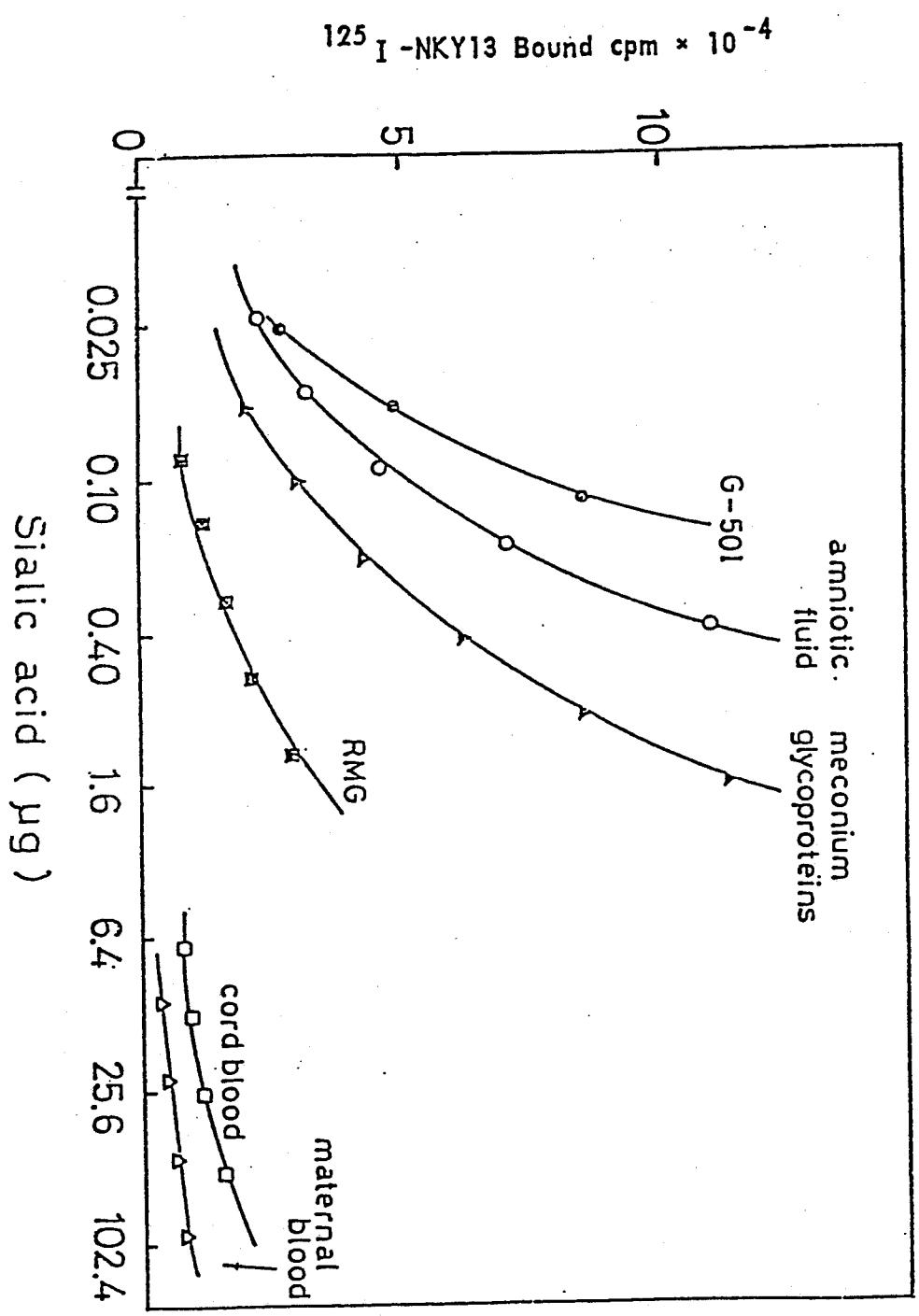
FIG. 1 shows the affinity of G-50I of SW1116, a glycoprotein of human amniotic fluid, a glycoprotein of human meconium, RMG, a glycoprotein of human cord blood and a glycoprotein of human maternal blood with the NKY13 adsorbed on polystyrene beads. The axis of ordinate shows a combining value of $^{125}$I-NKY13, and the axis of abscissa shows the quantity of an added test sample in terms of sialic acid.

From the above standpoint, a monoclonal antibody NKY13 was obtained by selecting a hybridoma that produces a monoclonal antibody which reacts with mucin-type glycopeptides prepared from SW1116 cells (ATCC CCL233) from a number of hybridomas obtained by fusing immunized mouse spleen cells with myeloma cells. Namely, one of the characteristics of this invention is that the antibody is a monoclonal antibody which reacts with sugar chains of glycoproteins, especially with sugar chains of mucin-type glycoproteins. Hitherto, it has been considered difficult to obtain this sort of an antibody.

The antibody of this invention reacts not only with a human intestinal cancer tissue but also with a normal tissue. This indicates that the antigen is not secreted in the sera of healthy persons but is secreted only in the sera of patients with various cancers.

The antibody of this invention slightly reacts with glycolipids extracted from SW1116 (ATCC CCL233), LS180 (ATCC CL-180) and human meconium. This suggests that the antigens which the antibody recognizes are mainly glycolipids on the surface of the cells and mucin-type glycoproteins in the sera of cancer patients. It is assumed that the antibody reacts with glycolipids as antigens in normal cells, which is the cause of its reactivity with normal cells, and as a result of canceration most of such sugar chains are linked to polypeptide chains to form mucin-type glycoproteins, which cover the surface of the cancer cells and is secreted out of the cells.

The antibody of this invention is different in terms of antigenic specificity from any of the previously known antibodies recognizing cancer-associated sugar chain antigens, for example, NS19-9 (mentioned above), CA50 (J. E. Monsson, et al., Biochim. et Biphys. Acta 834, 110 (1985)), FH9 (Y. Fukushi, et al., Biochemistry 25, 2859 (1986)), MLS102 (A. Kurosaka, et al., FEBS Letters 215, 137 (1987) and Japanese Patent Application No. 61-179757), etc.

The antibody of this invention furthermore reacts with glycoproteins contained in LS180 (ATCC CL-180), human meconium, human colostrum, human cord blood, human amniotic fluid, human semen, human saliva, etc., and also with oligosaccharides in human colostrum. This well corresponds with the fact that cancer-associated antigens are temporarily formed in the fetal period and called carcinoembryonic antigen. This also indicates that, like CA19-9, the mucin-type glycoprotein as an antigen is present not only in cancer cells but also in secretion juice of normal healthy persons.

In addition, the antibody of this invention reacts with the sugar chains of the following structures:

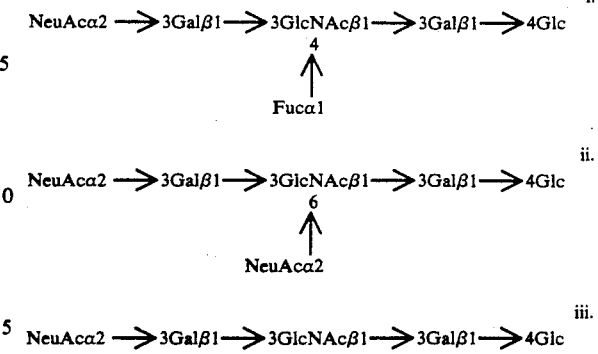

Furthermore, the oligosaccharide alcohol which is isolated from mucin-type glycoproteins by alkali treatment in the presence of a reducing agent also reacts with the antibody. This behavior presents striking contrast to the fact that where CA19-9 exists as sugar chains of mucin-type glycoproteins the oligosaccharide alcohol prepared by alkali treatment does not react with NS19-9.

The hybridoma which secretes the antibody is obtained by first fusing, in a usual manner, myeloma cells with spleen cells that are obtained from mice intraperitoneally immunized with human colonic cancer cells SW1116 and then by selecting clones which produce antibodies reactive with sugar chains of mucin-type glycopeptides previously prepared from SW1116 cells. The said hybridoma can stably be stored for a long period of time in 10% dimethylsulfoxide and 90% fetal calf serum (FCS) under cooling with liquid nitrogen (−198° C.). When needed, a required quantity of the hybridoma is defrosted, and it is cultured and proliferated in RPMI-1640 containing 20% FCS or in Dulbecco's minimum essential medium (MEM). After that it is inoculated into abdominal cavities of mice which are previously treated with pristane at about 0.5 ml per animal before 2 weeks to 3 months. Then, 10 days to 2 weeks after that, a large quantity of monoclonal antibody NKY13 can be obtained from the ascites. In this case, about 5 ml of ascites is obtained per mouse, from which 7-14 mg of the said antibody can steadily be obtained. This antibody in ascites, after being fractionated with ammonium sulfate, is dialyzed, and then passed through an affinity column such as Protein A-Sepharose 4B, whereby the antibody can easily be refined into a pure monoclonal antibody. In addition, monoclonal antibody NKY13 is also secreted in a culture medium of the said hybridoma in concentrations of 20–40 μg/ml after 3 days' culture, so this antibody in the culture medium can also be used.

The hybridoma of this invention has been deposited since May 26, 1987 with ECACC (European Collection of Animal Cell Cultures), Porton Down, Salisbury, Wiltshire SP4 OJG, England under the accession No. 87052601 in accordance with Budapest Treaty.

EXAMPLE

This invention is detailed in the following examples. However, it is not to intend restricting the scope of this invention.

EXAMPLE 1

Preparation of Hybridoma

SW1116 cells were used as immunogens, while Balb/c was used as mice to be immunized. SW1116 cells cultured in Eagle's medium containing 10% fetal calf serum were intraperitoneally administered to Balb/c 9 times over a period of 3 months, each time at a dose of $1-2\times10^6$ cells of SW1116 per mouse, which was suspended in 0.5 ml of physiological saline. Next, $1-2\times10^6$ cells of SW1116 suspended in 0.5 ml of physiological saline was intravenously administered to each of the aforesaid mice; and 3 days after that, spleen cells were obtained from the mice. In Dulbecco's culture medium not containing fetal serum $1.5\times10^8$ of the spleen cells and $2\times10^7$ of myeloma cells (SP2/0-Ag14) were mixed. And after washing the cells by centrifugation (1,000 rpm, 5 min), 0.5 ml of Dulbecco's culture medium not containing fetal calf serum, to which was added polyethylene glycol (PEG #1000) by 35%, was added thereto and mixed. The mixture was centrifuged at 1,000 rpm for 5 min, whereby spleen cells and myeloma cells were fused together. It was diluted with 5 ml of Dulbecco's culture medium not containing fetal calf serum and 5 ml of Dulbecco's culture medium containing 20% fetal calf serum, and then was centrifuged (1,000 rpm, 5 min) for removing the PEG used in the fusion. The cells from which the PEG was removed were suspended in 50 ml of 72% Dulbecco's culture medium and 8% NCTC109 culture medium (HT medium), and then was distributed dropwise (about 0.1 ml) to a 96-well tissue culture plate, after which it was cultured for 24 hr. A drop of HT culture medium containing 0.8 μM of aminopterin was added to each well on the culture plate to make it HAT medium. Hybridomas obtained by the fusion were cultured in the HAT medium so as to isolate them from the spleen cells and myeloma cells which did not fuse together. About 10 days after the cell fusion, the supernatant was collected from each well, and the reactivity with G-50I (See Referential Example) immobilized to wells was examined by the method shown in Example 4. The wells containing clones which reacted with G-50I were subjected to 2 more cloning procedures by dilution method, and 14 kinds of hybridomas were finally obtained. From these 14 hybridomas was selected such a clone as strongly reacts with G-50I but does not react with G-50II and scarcely reacts with glycolipids, and the clone thus selected was named NKY13.

EXAMPLE 2

Preparation and Purification of Monoclonal Antibody

Pristane is intraperitoneally administered to Balb/c mice at 0.5 ml per mouse. About one month after that, NKY13-secreting hybridomas which was cultured in a hybridoma proliferation medium consisting of 10% Dulbecco's culture medium, 10% NCTC109 culture medium and 20% fetal calf serum is intraperitoneally administered to the mice at a dose of $10^7$ cells per mouse, which is suspended in 0.5 ml of Hanks' physiological salt solution. About 10 days later, ascites are obtained from the mice. In this case, about 5-7 ml of ascites are obtainable per mouse, which contains about 10 mg of NKY13. Ammonium sulfate is added to the ascites so as to finally make it 50% saturation. This is then centrifuged, and the precipitate is dissolved in 0.1M borate buffer solution (pH 8.2) (Buffer A), and the solution thus obtained is dialyzed against the buffer. Then, the testing sample, being divided into several portions, is subjected to a column of Protein A-Sepharose CL-4B, and the column is washed with Buffer A. The column is previously equilibrated with Buffer A and contains 6 ml of resin. This column can adsorb about 30 mg of IgG. Antibody adsorbed to the column is eluted with 0.1M acetic acid containing 0.15M sodium chloride. The eluate is neutralized with 1M Tris. Ammonium sulfate is added to the eluate so as to make it 50% saturation. The precipitate obtained by centrifugation is dissolved in Buffer A, which is then dialyzed against Buffer A to obtain antibody NKY13.

EXAMPLE 3

Reactivity of Monoclonal Antibody NKY13 with Tissues of Human Intestinal Cancer Tissues of human intestinal cancer fixed with formalin are dehydrated and embedded in paraffin. Then the tissues are cut into slices, after which paraffin is removed from the slices with xylene. The slices are further washed with alcohol for removing xylene. Lastly, the tissue slices are washed with phosphate buffered saline (PBS) and immersed in PBS. Then, the slices are allowed to react overnight with monoclonal antibody NKY13. After being washed, the slices are allowed to react with anti-mouse IgG antibody which is labelled with fluorescein isothiocyanate (FITC) and FITC-IgG not combined is removed by washing, and the parts reacting with NKY13 are examined with a fluorescence microscope. Unlike MLS102, NKY13 reacts with both cancerous parts and normal parts.

EXAMPLE 4

Reactivity of Monoclonal Antibody NKY13 with Mucin-Type Glycopeptide

Bovine serum albumin (1%) is added to wells of poly(vinyl chloride) on which, through the mediation of polylysine and glutaraldehyde, is immobilized mucin-type glycopeptide (G-50I) that is isolated from human intestinal cancer cells SW1116 or LS180. After allowing it to stand for 1 hr, the wells are washed, and then a monoclonal antibody NKY13 is added thereto and allowed to react overnight. After washing the wells, Protein A labelled with $^{125}I$ is added, which is allowed to react for 2 hr. After washing the wells, the affinity of NKY13 is measured, taking as index the radioactivity of $^{125}I$ combined with the well. Then, it is found that NKY13 binds to G-50I. A test using G-50I from which sialic acid was removed was performed in the same way as mentioned above, but NKY13 did not show any affinity. From this, it is revealed that NKY13 reacts with the sugar chains of mucin-type glycopeptides which contains sialic acid.

The affinity of NKY13 can also be measured by using polystyrene beads coated with NKY13. Polystyrene beads (EP-03, #80, Sekisui) are washed with phosphate buffered saline (pH 7.4) (PBS) containing 0.15M sodium chloride. To coat the beads with the antibody, the beads are allowed to stand overnight at 4° C. in PBS containing 0.1 mg/ml of NKY13. Then, the beads are washed 3 times with PBS containing 5% bovine serum albumin (BSA), after which the beads are immersed in the solution, and allowed to stand for 1 hr. The solution is removed by suction, and to the beads are added 100 μl of testing sample (containing SW1116-derived G-50I), 50 μl of PBS containing 0.2% Tween 20 and 50 μl of PBS containing 12.5 ng of $^{125}$I-NKY13 and 0.1% BSA (about 200,000 count), which is allowed to stand overnight at 4° C. after being well mixed. Next, the beads are washed 3 times with PBS and the affinity of the antibody is calculated by measuring, with a γ-counter, the radioactivity combined with the beads (FIG. 1).

EXAMPLE 5

Reactivity of Monoclonal Antibody NKY13 with Various Mucin-Type Glycoproteins The reactivity of NKY13 with amniotic fluid, cord blood and maternal blood of normal human was examined by using polystyrene beads in accordance with the procedure in Example 4. The results are shown in FIG. 1.

Rectal mucin-type glycoprotein (RMG) was prepared from intestinal cancer tissues by the method of H. Nakajima, et al. (J. Biochem. 93, 651 (1983)) and most of the structure of its sugar chains has been determined (A. Kurosaka et al, J. Biol. Chem. 258, 11594 (1983)).

Glycoprotein of human meconium was prepared in the following manner. In 10 ml of water 1.9 g of human meconium was suspended. To this was added 90 ml of a mixture of chloroform/methanol (2:1, v/v). After being stirred well, it was allowed to stand. Then, the solution divided into two layers, that is, the organic lower layer and the aqueous upper layer. The upper layer was evaporated to dryness, which was extracted 3 times with the same mixture of chloroform/methanol. The extracted solution was combined with the lower layer of the first extraction, which was evaporated to dryness to give a glycolipid fraction of the human meconium. Water was added to the residue of the extraction, and after being stirred, it was centrifuged to remove impurities. The resulting supernatant was taken as a glycoprotein fraction of the human meconium. The reactivity of this glycoprotein fraction with NKY13 was examined using polystyrene beads in accordance with the procedure mentioned in Example 4. The results are shown in FIG. 1.

The reactivity of NKY13 with human colostrum, human semen and human saliva was examined in the same way as above to give the results as shown in Table 1.

EXAMPLE 6

Reactivity of Monoclonal Antibody NKY13 with Various Glycolipids

Bovine and swine brains, SW1116 cells and LS180 cells each is homogenized in water at 4° C. by a Downs type homogenizer. To the homogenate are added methanol and chloroform in such a way that the final concentration of chloroform/methanol/water reaches 2.7:5.4:2, v/v. Then, it is stirred at room temperature for 30 min for extracting glycolipid. After centrifugation, 2 volume parts of water are added to the precipitate, which is homogenized. To this 8 volume parts of a mixture of chloroform/methanol (1:2, v/v) are added, stirred for extracting glycolipid, and centrifuged to give extracts. After filtering 2 extracts with Celite 535, these are mixed in a separating funnel. And then water is added thereto in such a way that the ratio of chloroform/methanol/water comes to 1:2:2.4, v/v. After being stirred gently, the solution is allowed to stand. The resulting upper layer is removed, and to the lower layer is added methanol 3 times as much as water. After stirring well, 0.001M potassium chloride is added in 2 parts by volume for 1 part of the lower layer, which, after being stirred slowly, is allowed to stand overnight, and the resulting supernatant is recovered. This supernatant is combined with the aforementioned supernatant, to which is added isobutanol. And the solution is evaporated to dryness under reduced pressure. This dried preparation is stirred overnight in a mixture of chloroform/methanol/water (60:30:4.5, v/v), after which impurities are removed by centrifugation, and the resulting supernatant is evaporated to dryness. The dried preparation is dialyzed against a small quantity of water. After dialysis, the resultant is dried and then dissolved in methanol. Impurities are removed by centrifugation and the resulting supernatant is used as a glycolipid fraction.

As regards a glycolipid fraction of human meconium, the preparation obtained in Example 5 is used.

Methanol is added to each glycolipid fraction in such a way that the glycolipid contained in 1 mg (wet weight) of the starting material is dissolved in 20 μl of methanol. Next, 20 μl of the said methanol solution is added to each well of poly(vinyl chloride), and the methanol is evaporated under reduced pressure so that the glycolipid is coated on the surface of the well, to which is added 1% bovine serum albumin and incubated for 30 min. After the wells are washed, monoclonal antibody NKY13 is added thereto and allowed to react for 3 hr at room temperature. After being washed, $^{125}$I-Protein A is added and allowed to react for 2 hr. After that, the wells are washed and the affinity of the antibody is measured from the radioactivity combined with the well. As a result, it is found that the antibody reacts with glycolipids of SW1116 cells and LS180 cells, and slightly reacts with glycolipid of human meconium, but does not react with other glycolipids (Table 1).

EXAMPLE 7

Structure of Sugar Chains Recognized by Monoclonal Antibody NKY13

Structure of sugar chains recognized by monoclonal antibody NKY13 was investigated on the basis of the inhibition of the binding of the NKY13 to G-50I by the following sugar chains according to the above method. The same test was performed on NS19-9. The results are shown below.

| | 50% INHIBITION (μM) | |
|---|---|---|
| INHIBITOR | NKY13 | NS19-9 |
| NeuAcα2 ⟶ 3Galβ1 ⟶ 3GlcNAcβ1 ⟶ 3Galβ1 ⟶ 4Glc<br>4<br>↑<br>Fucα1 | 1.86 | 11.1 |

-continued

| INHIBITOR | 50% INHIBITION (μM) | |
|---|---|---|
| | NKY13 | NS19-9 |
| NeuAcα2 →3Galβ1 →3GlcNAcβ1 →3Galβ1 →4Glc<br>　　　　　　　　　　6<br>　　　　　　　　　　↑<br>　　　　　　　　NeuAcα2 | 320 | 3550 |
| NeuAcα2 →3Galβ1 →3GlcNAcβ1 →3Galβ1 →4Glc | 320 | 3550 |
| Galβ1 →3GlcNAcβ1 →3Galβ1 →4Glc<br>　　　　　6<br>　　　　　↑<br>　　　NeuAcα2 | *— | — |
| NeuAc or NeuGc | 9000 | — |
| Galβ1 →3GlcNAcβ1 →3Galβ1 →4Glc<br>　　　　　4<br>　　　　　↑<br>　　　Fucα1 | — | 2320 |
| Galβ1 →3GlcNAcβ1 →3Galβ1 →4Glc<br>　2　　　　　4<br>　↑　　　　　↑<br>Fucα1　　　Fucα1 | — | — |
| Galβ1 →3GlcNAcβ1 →3Galβ1 →4Glc | — | — |
| Galβ1 →4GlcNAcβ1 →3Galβ1 →4Glc<br>　　　　　3<br>　　　　　↑<br>　　　Fucα1 | — | — |
| L-Fucose | — | 14000 |

*—: No inhibition was observed at 10000 μM.

TABLE 1

| Reactivity of NKY13 | |
|---|---|
| Testing sample | Reactivity |
| G-50I (SW1116) | ++ |
| G-50I (LS180) | ++ |
| RMG | + |
| Glycoprotein in human amniotic fluid | ++ |
| Glycoprotein in human meconium | ++ |
| Glycoprotein in human cord blood | + |
| Glycoprotein of human maternal blood | ± |
| Human colostrum (Oligosaccharide) | ++ |
| Glycoprotein in human semen | + |
| Glycoprotein in human saliva | + |
| Glycolipid of SW1116 | + |
| Glycolipid of LS180 | + |
| Glycolipid in human meconium | ± |
| Glycolipid in bovine brain | — |
| Glycolipid in swine brain | — |

As shown in Table 1 above, NKY13 weakly binds to glycolipids isolated from SW1116 and LS180, binds slightly to glycolipids from human meconium, and does not bind to those glycolipids from bovine brain and swine brain.

EXAMPLE 8

Assay of NKY13 Antigenic Titer in Sera of Cancer Patients

Figure 3:
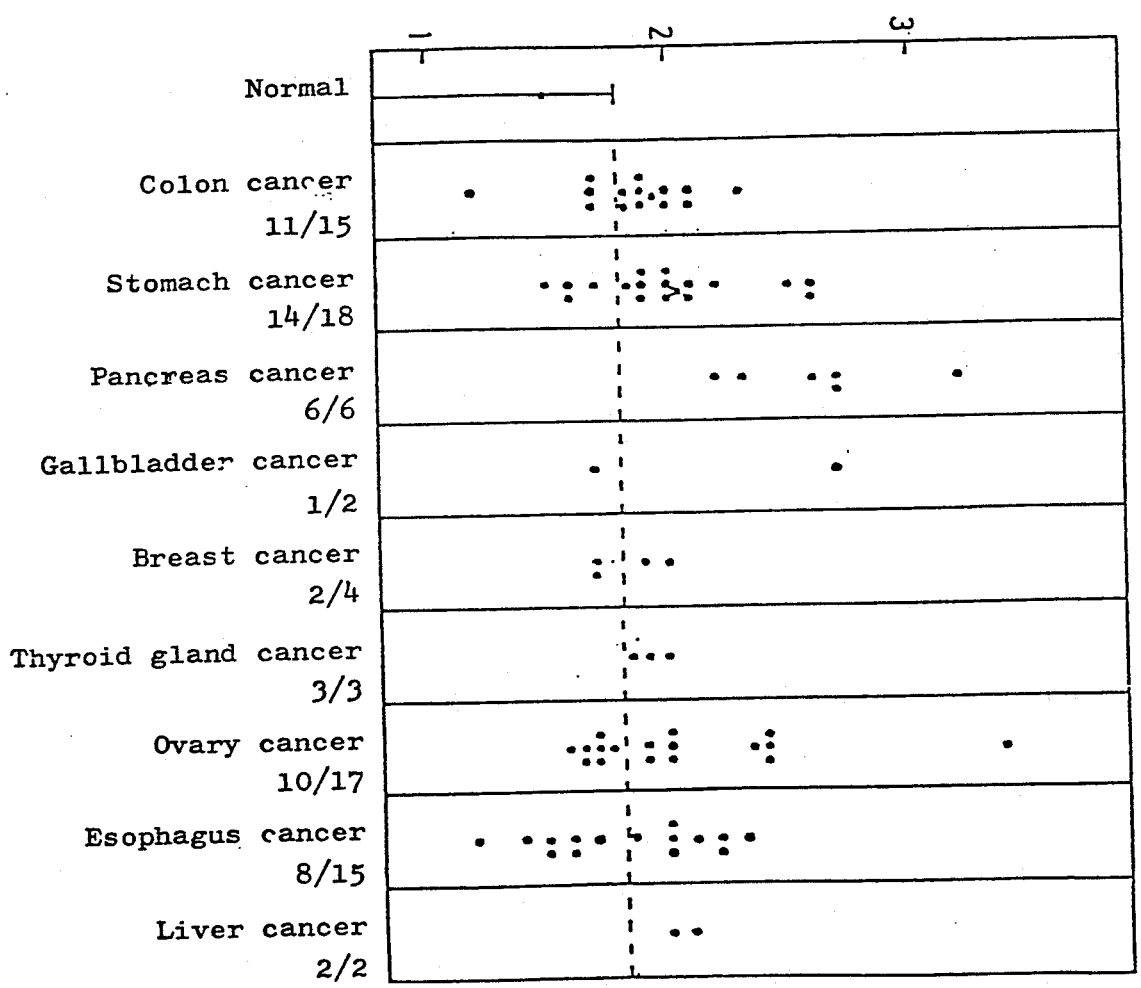
FIG. 3 shows NKY13 antigenic titer in sera of normal persons and also of patients with various cancers.

According to the method described in Example 4 using polystyrene beads, NKY13 antigenic titers in sera of normal persons and also of patients with various cancers were measured and the results are shown in FIG. 3. The NKY13 antigenic titer was especially high in sera of patients with colon cancer, stomach cancer and pancreas cancer. This indicates that the monoclonal antibody NKY13 is effective in the diagnosis of these cancers.

Referential Example: Preparation of G-50I

Figure 2:
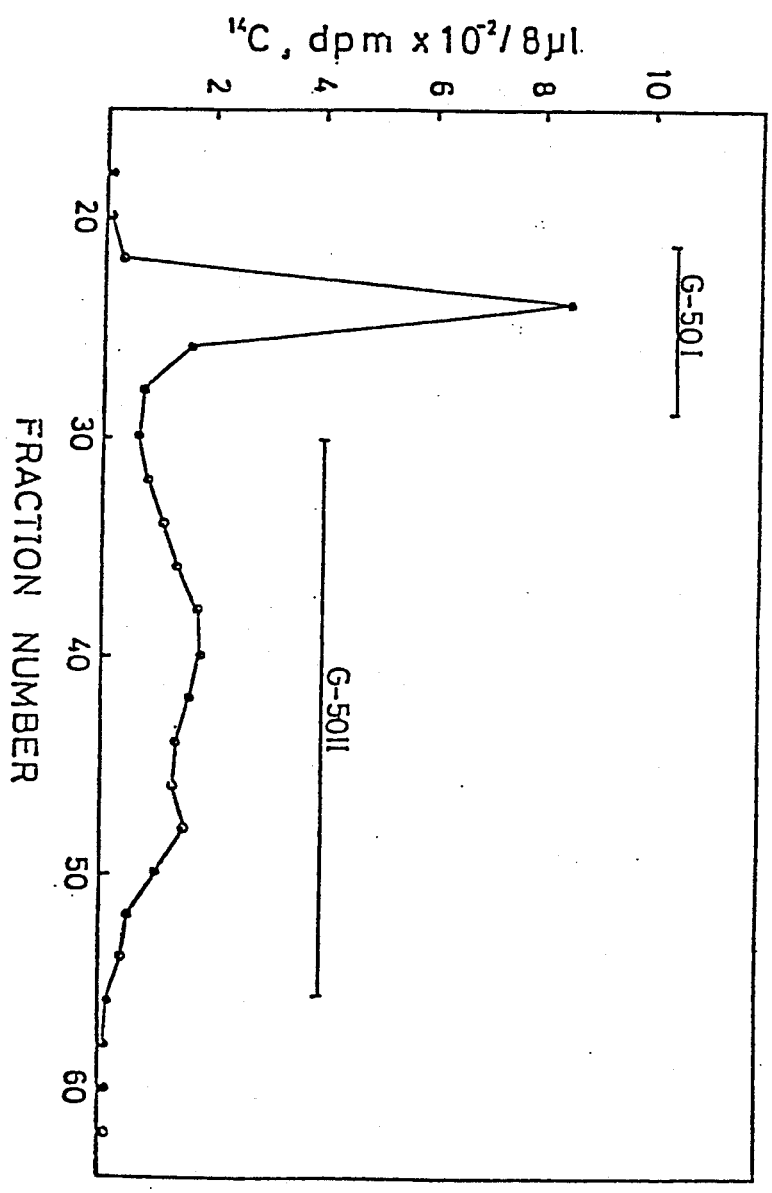
FIG. 2 shows the relationship between fraction numbers (axis of abscissa) of eluted fractions of G-50I and G-50II of SW1116 and radioactivity of [$^{14}$C] glucosamine (dpm×10⁻²/8 μl, axis of ordinate). [¹⁴C] glucosamine is added to the culture medium when SW1116 is being cultured, and is made to be incorporated into amino sugar and sialic acid of glycoproteins of cells.

G-50I is a glycopeptide prepared from a mucin-type glycoprotein which constitutes cell membranes (plasma membranes) of human intestinal cancer cells SW1116 (ATCC CCL233) and LS180 (ATCC CL-187) and which is secreted out of the cells. It is prepared as follows:

Human intestinal cancer cells SW1116 (ATCC CCL233) are cultured for 7 days in Dulbecco's medium containing 10% fetal calf serum. The cultured cells are collected and washed repeatedly with phosphate buffered saline (137 mM sodium chloride, 2.7 mM potassium chloride, 8.1 mM sodium monohydrogen phosphate, 1.5 mM potassium dihydrogen phosphate, 1.0 mM potassium chloride and 0.5 mM magnesium chloride. Hereinafter referred to as PBS.). After that, PBS containing 1% Triton X-100 (made by Rohm & Haas) is added, and stirred under cooling with ice. Then, it is centrifuged, and the resulting supernatant is dialyzed and then freeze-dried. The dried preparation is defatted with chloroform/methanol (2:1, v/v) and then suspended in acetate buffer solution containing 0.01M calcium acetate. To this is added Pronase P (made by Kaken Pharmaceutical) one fiftieth as much as the dried preparation and then added a small quantity of toluene, which is allowed to stand at 37° C. for 3 days for sufficient protein digestion. To the cell-digested solution which has become nearly transparent is added an equal quantity of 10% aqueous solution of trichloroacetic acid, and after being stirred, it is allowed to stand. The resulting insoluble substance is removed by centrifugation. To the supernatant is added an equal quantity of ether, and, after being mixed well, the supernatant is removed by centrifugation. To the aqueous layer is added ether, from which trichloroacetic acid is extracted, followed by centrifugation: this procedure is repeated 3 times. And after confirming that the aqueous layer has become ph 5, the resultant is applied to a column (1.3×60 cm) of Sephadex G-25 which is previously equilibrated with 0.5M pyridine-acetate buffer (pH 5.0). It is then eluted with the same buffer, and the eluate is collected by a fraction collector. The fractions positive to the orcinol-acetic acid reaction are collected and then freeze-dried. The dried powder obtained is dissolved in 0.5M pyridine-acetate buffer (pH 5.0), after which the solution is subjected to a gel filtration in the same way as above, using Sephadex G-50, and fractionated by a fraction collector in portions of 5 ml each. The fraction (G-50I) which passes through this step contains, as main component, a glycopeptide derived from a mucin-type glycoprotein (O-glycoside type). FIG. 2 shows the relationship between fraction number (axis of abscissa) and radioactivity of $[^{14}C]$ glucosamine (dpm×$10^{-2}$/8 μl, axis of ordinate).

Fractions 20–29 are collected, and the solvent is removed by freeze-drying to obtain mucin-type glycopeptide G-50I.

In this connection, fractions 30–56 contain a glycopeptide derived from serum-type glycoprotein (N-glycoside type), and this serum-type glycopeptide is named G-50II. The G-50I and G-50II can also be prepared in the same way as above from intestinal cancer cells LS180 (ATCC CL-187).

What we claim is:

1. Hybridoma NKY 13 deposited with the ECACC having the accession No. 87052601.

2. A monoclonal antibody NKY 13 which is produced by the hybridoma deposited with the ECACC under the accession No. 87052601.

* * * * *